US008057823B2

(12) United States Patent
Heurtault et al.

(10) Patent No.: US 8,057,823 B2
(45) Date of Patent: Nov. 15, 2011

(54) LIPID NANOCAPSULES, PREPARATION PROCESS AND USE AS MEDICINE

(75) Inventors: Béatrice Heurtault, Angers (FR); Patrick Saulnier, Les-Ponts-de-Ce (FR); Jean-Pierre Benoit, Avrille (FR); Jacques-Emile Proust, Saint-Leger-des-Bois (FR); Brigitte Pech, Angers (FR); Joël Richard, Longue (FR)

(73) Assignees: Universite d'Angers, Angers (FR); Ethypharm S.A., Saint-Cloud (FR)

( * ) Notice: Subject to any disclaimer, the term of this patent is extended or adjusted under 35 U.S.C. 154(b) by 1128 days.

(21) Appl. No.: 10/220,506

(22) PCT Filed: Mar. 2, 2001

(86) PCT No.: PCT/FR01/00621
§ 371 (c)(1), (2), (4) Date: Nov. 26, 2002

(87) PCT Pub. No.: WO01/64328
PCT Pub. Date: Sep. 7, 2001

(65) Prior Publication Data
US 2003/0152635 A1    Aug. 14, 2003

(30) Foreign Application Priority Data
Mar. 2, 2000 (FR) .................... 00 02688

(51) Int. Cl.
*A61K 9/16* (2006.01)
*A61K 9/14* (2006.01)

(52) U.S. Cl. ........ 424/498; 424/450; 424/489; 424/490; 424/502

(58) Field of Classification Search ................ 424/489, 424/450, 490, 502
See application file for complete search history.

(56) References Cited

U.S. PATENT DOCUMENTS

| | | | |
|---|---|---|---|
| 4,235,871 A * | 11/1980 | Papahadjopoulos et al. | 424/450 |
| 5,049,322 A | 9/1991 | Devissaguet et al. | |
| 5,174,930 A | 12/1992 | Stainmesse et al. | |
| 5,514,670 A * | 5/1996 | Friedman et al. | 514/2 |
| 5,556,617 A * | 9/1996 | Ribier et al. | 424/78.02 |
| 5,576,016 A * | 11/1996 | Amselem et al. | 424/450 |
| 5,723,137 A * | 3/1998 | Wahle et al. | 424/401 |
| 5,961,970 A * | 10/1999 | Lowell et al. | 424/93.1 |
| 5,972,389 A * | 10/1999 | Shell et al. | 424/501 |
| 5,993,831 A * | 11/1999 | Ribier et al. | 424/401 |
| 6,066,328 A * | 5/2000 | Ribier et al. | 424/401 |
| 6,121,313 A * | 9/2000 | Gao et al. | 514/459 |
| 6,242,099 B1 * | 6/2001 | Grandmontagne et al. | 428/402.2 |
| 6,245,349 B1 * | 6/2001 | Yiv et al. | 424/450 |
| 6,248,363 B1 * | 6/2001 | Patel et al. | 424/497 |
| 2001/0010824 A1 | 8/2001 | Handjani et al. | |

FOREIGN PATENT DOCUMENTS

| | | |
|---|---|---|
| EP | 0 529 711 | 3/1991 |
| EP | 0 621 073 | 10/1994 |
| EP | 0 447 318 | 5/1995 |
| EP | 0 646 002 | 12/1995 |
| EP | 0 717 989 | 6/1996 |
| EP | 0 717 989 A1 * | 6/1996 |
| WO | WO91/07171 * | 5/1991 |

OTHER PUBLICATIONS

Magalhaes NS, et al: An Invitro kinetic exam and comparative evaluation between submicron emulsion and polylactic acid nanocapsules of clofibride; J. Microencapsul. Mar.-Apr. 1995; 12(2): 195-205.*
Aboubakar, M et al: Study of the mechanism of insulin encapsulation in poly(isobutylcyanoacrylate) nanocapsules obtained ny interfacial polymerization: J. Biomed Mater Res. Dec. 15, 1999; (4): 568-576.*
Magalhaes et al, J. Microencapsul. Mar.-Apr. 1995; 12(2): 195-205.*
Aboubaker et al, J. biomed Mater Res. Dec. 15, 1999; 47(4): 568-576.*
Anton et al., "The universality of low-energy nano-emulsification," *International Journal of Pharmaceutics*, vol. 377, pp. 142-147, 2009.
Anton et al., "Design and Production of nanoparticles formulated from nano-emulsion templates—A review," *Journal of Controlled Release*, vol. 128, pp. 188-199, 2008.

* cited by examiner

*Primary Examiner* — Michael G Hartley
*Assistant Examiner* — Micah-Paul Young
(74) *Attorney, Agent, or Firm* — Foley & Lardner LLP

(57) ABSTRACT

The invention concerns nanocapsules, in particular with an average size less than 50 nm, consisting of an essentially lipid core liquid or semiliquid at room temperature, coated with an essentially lipid film solid at room temperature having a thickness of 2-10 nm. The invention also concerns a method for preparing same which consists in producing a reverse phase of an aqueous emulsion brought about by several temperature raising and lowering cycles. Said lipid nanocapsules are particularly designed for producing a medicine.

18 Claims, 2 Drawing Sheets

LIPID NANOCAPSULES, PREPARATION PROCESS AND USE AS MEDICINE

The present invention relates to lipid nanocapsules, to a process for preparing them and to their use for manufacturing a medicament intended especially to be administered by injection, orally or nasally.

In recent years, many groups have developed the formulation of solid lipid nanoparticles or lipid nanospheres (Müller, R. H. and Mehnert, European Journal of Pharmaceutics and Biopharmaceutics, 41(1): 62-69, 1995; W., Gasco, M. R., Pharmaceutical Technology Europe: 52-57, December 1997; EP 605 497). This is an alternative to the use of liposomes or polymer particles. These lipid particles have the advantage of being formulated in the absence of solvent. They allow the encapsulation of both lipophilic and hydrophilic products in the form of ion pairs, for example (Cavalli, R. et al., S.T.P. Pharma Sciences, 2(6): 514-518, 1992; and Cavalli, R. et al., International Journal of Pharmaceutics, 117: 243-246, 1995). These particles may be stable for several years in the absence of light, at 8° C. (Freitas, C. and Müller, R. H., Journal of Microencapsulation, 1 (16): 59-71, 1999).

Two techniques are commonly used to prepare lipid nanoparticles:
homogenization of a hot emulsion (Schwarz, C. et al., Journal of Controlled Release, 30: 83-96, 1994; Müller, R. H. et al., European Journal of Pharmaceutics and Biopharmaceutics, 41(1): 62-69, 1995) or of a cold emulsion (Zur Mühlen, A. and Mehnert W., Pharmazie, 53: 552-555, 1998; EP 605 497), or
the quench of a microemulsion in the presence of co-surfactants such as butanol. The size of the nanoparticles obtained is generally greater than 100 nm (Cavalli, R. et al., European Journal of Pharmaceutics and Biopharmaceutics, 43(2): 110-115, 1996; Morel, S. et al., International Journal of Pharmaceutics, 132: 259-261, 1996).

Cavalli et al. (International Journal of Pharmaceutics, 2(6): 514-518, 1992; and Pharmazie, 53: 392-396, 1998) describe the use of a nontoxic bile salt, taurodeoxycholate, by injection for the formation of nanospheres greater than or equal to 55 nm in size.

The present invention relates to nanocapsules rather than nanospheres. The term "nanocapsules" means particles consisting of a core that is liquid or semiliquid at room temperature, coated with a film that is solid at room temperature, as opposed to nanospheres, which are matrix particles, ie particles whose entire mass is solid. When the nanospheres contain a pharmaceutically active principle, this active principle is finely dispersed in the solid matrix.

In the context of the present invention, the term "room temperature" means a temperature between 15 and 25° C.

One subject of the present invention is nanocapsules with an average size of less than 150 nm, preferably less than 100 nm and more preferably less than 50 nm. The nanocapsules each consist of an essentially lipid core that is liquid or semiliquid at room temperature, coated with an essentially lipid film that is solid at room temperature.

Given their size, the nanocapsules of the invention are colloidal lipid particles.

The polydispersity index of the nanocapsules of the invention is advantageously between 5% and 15%.

The thickness of the solid film is advantageously between 2 and 10 nm. It is also about one tenth of the diameter of the particles.

The core of the nanocapsules consists essentially of a fatty substance that is liquid or semiliquid at room temperature, for example a triglyceride or a fatty acid ester, representing 20% to 60% and preferably 25% to 50% by weight of the nanocapsules.

The solid film coating the nanocapsules preferably consists essentially of a lipophilic surfactant, for example a lecithin whose proportion of phosphatidylcholine is between 40% and 80%. The solid film may also contain a hydrophilic surfactant, for example Solutol® HS 15.

The hydrophilic surfactant contained in the solid film coating the nanocapsules preferably represents between 2% and 10% by weight of the nanocapsules, preferably about 8%.

The triglyceride constituting the core of the nanocapsules is chosen especially from $C_8$ to $C_{12}$ triglycerides, for example capric and caprylic acid triglycerides and mixtures thereof.

The fatty acid ester is chosen from $C_8$ to $C_{18}$ fatty acid esters, for example ethyl palmitate, ethyl oleate, ethyl myristate, isopropyl myristate, octyldodecyl myristate, and mixtures thereof. The fatty acid ester is preferably $C_8$ to $C_{12}$.

The nanocapsules of the invention are particularly suitable for formulating pharmaceutical active principles. In this case, the lipophilic surfactant may advantageously be solid at 20° C. and liquid at about 37° C.

The amount of lipophilic surfactant contained in the solid film coating the nanocapsules is set such that the liquid fatty substance/solid surfactant compound mass ratio is chosen between 1 and 15, preferably between 1.5 and 13 and more preferably between 3 and 8.

A subject of the present invention is also a process for preparing the nanocapsules described above.

The process of the invention is based on the phase inversion of an oil/water emulsion brought about by several cycles of raising and lowering temperature.

The process of the invention consists in
a) preparing an oil/water emulsion containing an oily fatty phase, a nonionic hydrophilic surfactant, a lipophilic surfactant that is solid at 20° C. and optionally a pharmaceutically active principle that is soluble or dispersible in the oily fatty phase, or a pharmaceutically active principle that is soluble or dispersible in the aqueous phase,
bringing about the phase inversion of said oil/water emulsion by increasing the temperature up to a temperature $T_2$ above the phase inversion temperature (PIT) to obtain a water/oil emulsion, followed by a reduction in the temperature down to a temperature $T_1$, $T_1 < PIT < T_2$,
carrying out at least one or more temperature cycles around the phase inversion zone between $T_1$ and $T_2$, until a translucent suspension is observed,
b) quenching the oil/water emulsion at a temperature in the region of $T_1$, preferably greater than $T_1$, to obtain stable nanocapsules.

The nanocapsules obtained according to the process of the invention are advantageously free of co-surfactants, for instance $C_1$-$C_4$ alcohols.

The number of cycles applied to the emulsion depends on the amount of energy required to form the nanocapsules.

The phase inversion may be visualized by canceling out the conductivity of the formation when the water/oil emulsion is formed.

The process of the invention comprises two steps.

The first step consists in weighing all the constituents, heating them above a temperature $T_2$ with gentle stirring (for example magnetic stirring) and then optionally cooling them to a temperature $T_1$ ($T_1 < T_2$). After a certain number of temperature cycles, a water/oil emulsion is obtained.

The phase inversion between the oil/water emulsion and the water/oil emulsion is reflected by a reduction in the conductivity when the temperature increases until it is canceled out. The average temperature of the phase inversion zone corresponds to the phase inversion temperature (PIT). The organization of the system in the form of nanocapsules is reflected visually by a change in the appearance of the initial system, which changes from opaque-white to translucent-white. This change takes place at a temperature below the PIT. This temperature is generally between 6 and 15° C. below the PIT.

$T_1$ is a temperature at which the conductivity is at least equal to 90-95% of the conductivity measured at 20° C.

$T_2$ is the temperature at which the conductivity becomes canceled out.

The second step consists of a sudden cooling (or quench) of the oil/water emulsion to a temperature in the region of $T_1$, preferably above $T_1$, with magnetic stirring, by diluting it between threefold and tenfold using deionized water at 2° C.±1° C. added to the fine emulsion. The particles obtained are kept stirring for 5 minutes.

In one preferred embodiment, the fatty phase is a fatty acid triglyceride, the solid lipophilic surfactant is a lecithin and the hydrophilic surfactant is Solutol® HS15. Under these conditions, $T_1=60°$ C., $T_2=85°$ C. and the number of cycles is equal to 3.

The liquid substance/solid surfactant compound ratio is chosen between 1 and 15, preferably between 1.5 and 13 and more preferably between 3 and 8.

The oil/water emulsion advantageously contains 1% to 3% of lipophilic surfactant, 5% to 15% of hydrophilic surfactant, 5% to 15% of oily fatty substance and 64% to 89% of water (the percentages are expressed on a weight basis).

The higher the HLB value of the liquid fatty substance, the higher the phase inversion temperature. On the other hand, the HLB value of the fatty substance does not appear to have an influence on the size of the nanocapsules.

Thus, when the size of the triglyceride end groups increases, their HLB value decreases and the phase inversion temperature decreases.

The HLB value, or hydrophilic/lipophilic balance, is as defined by C. Larpent in Treatise K.342 of Editions TECHNIQUES DE L'INGENIEUR.

The particle size decreases when the proportion of hydrophilic surfactant increases and when the proportion of surfactants (hydrophilic and lipophilic) increases. Specifically, the surfactant brings about a decrease in the interface tension and thus a stabilization of the system, which promotes the production of small particles.

Moreover, the particle size increases when the proportion of oil increases.

According to one preferred embodiment, the fatty phase is Labrafac® WL 1349, the lipophilic surfactant is Lipoid® S 75-3 and the nonionic hydrophilic surfactant is Solutol® HS 15. These compounds have the following characteristics:

Labrafac® lipophile WL 1349 (Gattefossé, Saint-Priest, France). This is an oil composed of caprylic and capric acid ($C_8$ and $C_{10}$) medium-chain triglycerides. Its density is from 0.930 to 0.960 at 20° C. Its HLB value is about 1.

Lipoid® S 75-3 (Lipoid GmbH, Ludwigshafen, Germany). Lipoid® S 75-3 corresponds to soybean lecithin. Soybean lecithin contains about 69% phosphatidylcholine and 9% phosphatidylethanolamine. They are thus surfactant compounds. This constituent is the only constituent that is solid at 37° C. and at room temperature in the formulation. It is commonly used for the formulation of injectable particles.

Solutol® HS 15 (BASF, Ludwigshafen, Germany). This is a polyethylene glycol-660 2-hydroxystearate. It thus acts as a nonionic hydrophilic surfactant in the formulation. It may be used by injection (via the iv route in mice $LD_{50}>3.16$ g/kg, in rats $1.0<LD_{50}<1.47$ g/kg).

The aqueous phase of the oil/water emulsion may also contain 1% to 4% of a salt, for instance sodium chloride. Changing the salt concentration brings about a shift in the phase inversion zone. The higher the salt concentration, the lower the phase inversion temperature. This phenomenon will be advantageous for encapsulating hydrophobic heat-sensitive active principles. Their incorporation may be performed at a lower temperature.

The nanocapsules of the invention may advantageously contain an active principle and may form part of the composition of a medicament to be administered by injection, especially intravenous injection, orally or nasally.

When the active principle is sparingly soluble in the oily phase, a cosolvent is added, for example N,N-dimethylacetamide.

The nanocapsules of the invention are more particularly suitable for the administration of the following active principles:
antiinfectious agents, including antimycotic agents and antibiotics,
anticancer agents,
active principles intended for the Central Nervous System, which must cross the blood-brain barrier, such as antiparkinson agents and more generally active principles for treating neurodegenerative diseases.

The pharmaceutically active principle may be firstly soluble or dispersible in an oily fatty phase, and in this case it will be incorporated in the core of the nanocapsule. To do this, it is incorporated at the stage of the first step of preparing the oil/water emulsion which also contains the oily fatty phase, a nonionic hydrophilic surfactant and a lipophilic surfactant that is solid at 20° C.

The pharmaceutically active principle may also be of water-soluble nature or dispersible in an aqueous phase, and in such a case it will be bound to the surface of the nanocapsules only after the final phase of preparing the stable nanocapsules. Such a water-soluble active principle may be of any nature, including proteins, peptides, oligonucleotides and DNA plasmids. Such an active principle is attached to the surface of the nanocapsules by introducing said active principle into the solution in which are dispersed stable nanocapsules obtained after the process according to the invention. The presence of a nonionic hydrophilic surfactant promotes the interaction bonds between the water-soluble active principle and the free surface of the nanocapsules.

The water-soluble active principle may also be introduced into the aqueous phase during the first step of initial oil/water preparation.

The invention is illustrated by the examples that follow, with reference to FIGS. 1 to 4.

Figure 3:
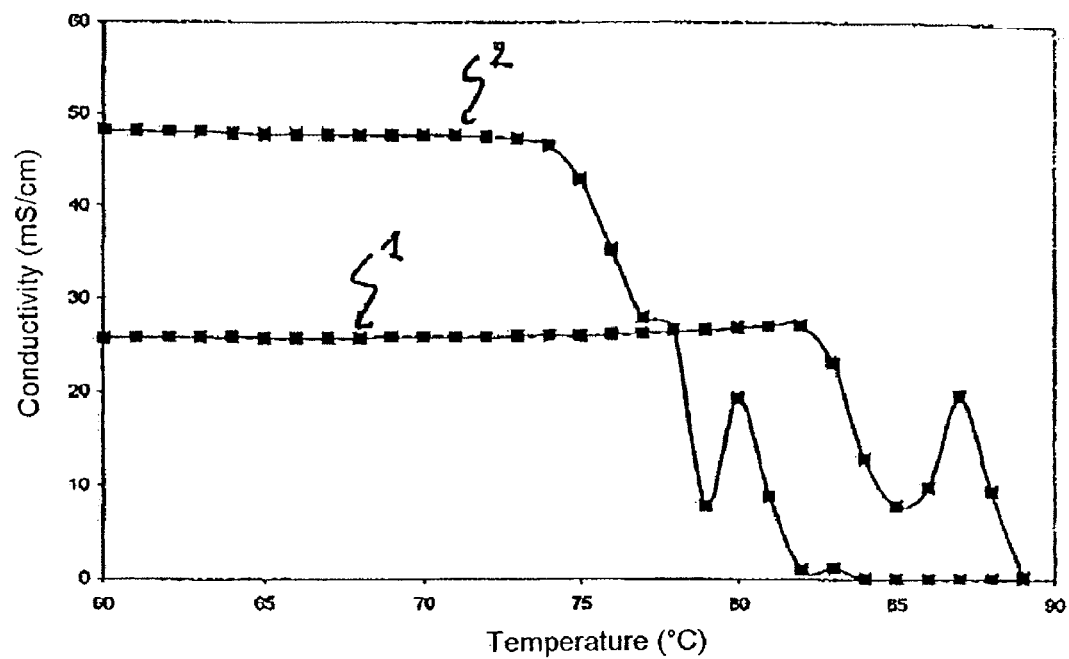

FIG. 3 shows the change in conductivity as a function of the temperature for various salt concentrations. In curve 1, the salt concentration is 2.0% by weight. In curve 2, the concentration is 3.4% by weight.

Figure 4:
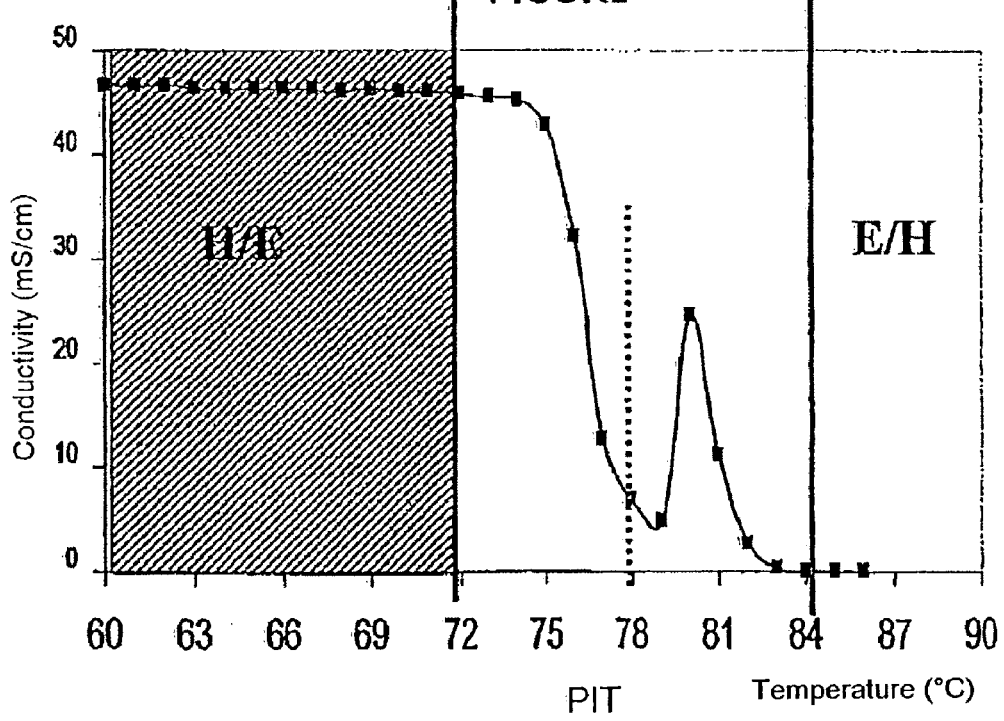

FIG. 4 shows the change in the conductivity of an oil/water (O/W) emulsion described in Example 1, as a function of the temperature after three cycles of raising and lowering the temperature between 60 and 85° C.

EXAMPLE 1

Nanocapsules not Containing Active Principle

A) Preparation of the Nanocapsules 5 g of an emulsion containing 75 mg of Lipoid® S75-3, 504 mg of Labrafac® WL 1349 lipophile, 504 mg of Solutol® HS 15, 3.829 g of water and 88 mg of sodium chloride are prepared.

The ingredients are combined in the same beaker and placed under magnetic stirring. Heat is applied until a temperature of 85° C. is reached. The system is allowed to cool to a temperature of 60° C. with magnetic stirring. This cycle (between 85° C. and 60° C.) is performed until a canceling out of the conductivity as a function of the temperature is observed (FIG. 4). The phase inversion takes place after three cycles. At the final cooling, quenching is carried out by adding 12.5 ml of distilled water at 2° C.±1° C. to the mixture at 70° C. The system is then maintained under magnetic stirring for 5 minutes.

Figure 1:
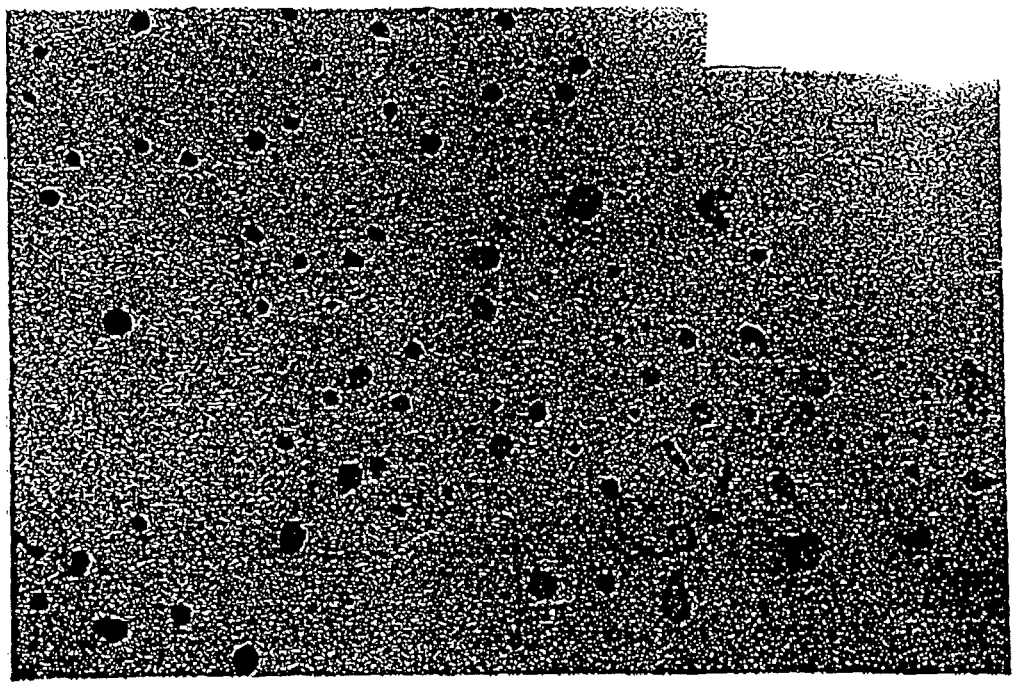
FIG. 1 is a photograph of the nanocapsules of the invention obtained in Example 1. The scale is 1 cm to 50 nm.

The particles obtained under the conditions described above, after three temperature cycles, have a mean size of 43±7 nm. Their size polydispersity is 0.071. Transmission electron microscopy using phosphotungstic acid made it possible to reveal particles with a mean size of about 50 nm (see FIG. 1). Moreover, an observation made by atomic force microscopy in contact mode (Park Scientific Instruments apparatus, Geneva, Switzerland) shows that the nanocapsules are indeed solid at a temperature of 25° C.

B) Change in the Proportions of Hydrophilic Surfactant

Table 1 below shows different formulations of nanocapsules prepared with variable concentrations of hydrophilic surfactant.

TABLE I

| | Mass % | | | | | | | |
|---|---|---|---|---|---|---|---|---|
| Lipoid S75-3 | 1.51 | 1.51 | 1.51 | 1.51 | 1.51 | 1.51 | 1.51 | 1.51 |
| Labrafac ® WL 1349 | 10.08 | 10.08 | 10.08 | 10.08 | 10.08 | 10.08 | 10.08 | 10.08 |
| Solutol ® HS 15 | 5.00 | 7.50 | 10.08 | 15.00 | 20.00 | 22.50 | 25.00 | 30.00 |
| Water | 81.65 | 79.10 | 76.60 | 71.68 | 66.68 | 64.18 | 61.68 | 56.68 |
| NaCl | 1.76 | 1.76 | 1.76 | 1.76 | 1.76 | 1.76 | 1.76 | 1.76 |

Figure 2:
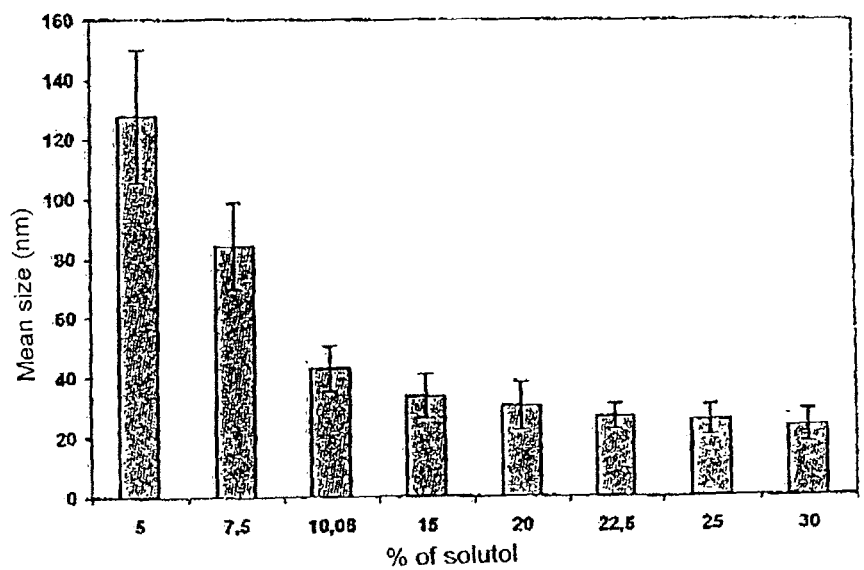
FIG. 2 shows the change in the average particle size as a function of the proportion of hydrophilic surfactant (Solutol®).

Decreasing the concentration of Solutol® HS 15 results in an increase in the mean particle size (FIG. 2). Mean sizes going from 23 to 128 nm are thus observed for Solutol® proportions going from 30% to 5% of the total formulation, respectively. The size thus depends on the concentration of hydrophilic surfactant.

C) Changes in the Proportions of Lipoid® and Solutol® Surfactants

Table II below shows formulations of nanocapsules prepared with various surfactant concentrations.

TABLE II

| | Mass % | | |
|---|---|---|---|
| | A | B | C |
| Lipoid ® S75-3 | 0.78% | 1.51% | 2.35% |
| Labrafac ® WL 1349 | 10.08% | 10.08% | 10.08% |
| Solutol ® HS 15 | 5.22% | 10.08% | 15.65% |
| Water | 82.16% | 76.60% | 70.16% |
| NaCl | 1.76% | 1.76% | 1.76% |
| Proportion of surfactants | 6.00% | 11.59% | 18.00% |

Increasing the proportion of surfactants in the formulation brings about a reduction in the mean size.

Specifically, formulation A gives particles with a mean size of 85±7 nm (P=0.124). For formulations B and C, the mean sizes become 43±7 nm (P=0.071) and 29±8 nm (P=0.148), respectively.

D) Change in the NaCl Concentration

Table III below shows two formulations of nanocapsules prepared with two different concentrations of NaCl salt.

TABLE III

| | Mass % | |
|---|---|---|
| Lipoid ® 375-3 | 1.73% | 1.70% |
| Labrafac ® WL 1349 | 5.76% | 2.84% |
| Solutol ® HS15 | 2.88% | 5.68% |
| Water | 87.61% | 86.36% |
| NaCl | 2.02% | 3.40% |

Changing the salt concentration brings about a shift in the phase inversion zone. The higher the salt concentration, the lower the phase inversion temperature (FIG. 3). This phenomenon will be advantageous for the encapsulation of hydrophobic heat-sensitive active principles. Their incorporation may be performed at a lower temperature.

With these formulations, particles similar in size to the previous sizes may be obtained, despite the different salt concentrations.

EXAMPLE 2

Encapsulation of a Lipophilic Active Principle, Sudan III

The formulation corresponds to that of Example 1: 5 g of the initial emulsion are prepared by weighing out 75 mg of Lipoid® S75-3, 504 mg of Labrafac® lipophile and 504 mg of Solutol®, 3.829 g of water and 88 mg of sodium chloride. 200 mg of Sudan III dissolved in liquid petroleum jelly are added. The mixture is weighed out in the same beaker and placed under magnetic stirring. Heat is applied until a temperature of 85° C. is reached. The system is allowed to cool to a temperature of 60° C. with magnetic stirring. This cycle (between 85° C. and 60° C.) is performed three times. At the final cooling, an quenching at 70° C. is carried out by adding 12.5 ml of distilled water at 2° C.±1° C. The system is then maintained under magnetic stirring for 5 minutes.

The encapsulation of Sudan III made it possible to obtain particles of a similar size to the particles of Example 1, for the same proportions of surfactants and of fatty phase, ie 45±12 nm (P=0.138). To the naked eye, the sample appears a uniform pink.

EXAMPLE 3

Encapsulation of Progesterone

The formulation corresponds to that of Example 1: 5 g of the initial emulsion are prepared by weighing out 75 mg of Lipoid® S75-3, 504 mg of Labrafac® lipophile and 504 mg of Solutol®, 3.829 g of water and 88 mg of sodium chloride. 10 mg of progesterone are added. The mixture is weighed out in the same beaker and placed under magnetic stirring. Heat is applied until a temperature of 85° C. is reached. The system is allowed to cool to a temperature of 60° C. with magnetic stirring. This cycle (between 85° C. and 60° C.) is performed three times. At the final cooling, an quenching at 70° C. is carried out by adding 12.5 ml of distilled water at 2° C.±1° C. The system is then maintained under magnetic stirring for 5 minutes.

The encapsulation of progesterone makes it possible to obtain particles of similar sizes to the particles of Example 1, ie 45±12 nm (P=0.112). The progesterone is not found in the aqueous phase at a concentration above its solubility. Specifically, a centrifugation at 200 000 rpm for 30 minutes gives a light precipitate whose composition was studied by DSC. This precipitate does not contain progesterone. Since progesterone is virtually insoluble in water, this indicates an incorporation of the active principle into the nanocapsules.

EXAMPLE 4

Encapsulation of a Busulfan Suspension

A) Suspension of Busulfan (at a Concentration of 0.25 mg/ml)

The first step of the encapsulation of busulfan consists in dissolving it in N,N-dimethylacetamide. A solution containing 24 mg of busulfan per ml of N,N-dimethylacetamide is thus prepared. 175 mg of this solution are taken and added to 504 mg of Labrafac®. 75 mg of Lipoid® S75-3, 504 mg of Solutol®, 3.829 g of water and 88 mg of sodium chloride are also weighed out. The initial emulsion is thus at a concentration of 0.88 mg/g of emulsion. The ingredients are combined in the same beaker and placed under magnetic stirring. Heat is applied until a temperature of 85° C. is reached. The system is allowed to cool to a temperature of 60° C. with magnetic stirring. This cycle (between 85° C. and 60° C.) is performed three times. At the final cooling, an quenching at 70° C. is carried out by adding 12.5 ml of distilled water at 2° C.±1° C. The system is then maintained under magnetic stirring for 5 minutes. The final concentration, ie after quenching, that is to say dilution, is 0.25 mg/ml.

The size of the particles obtained is slightly larger than that of Example 1 on account of the higher proportion of fatty phase (63±5 nm). As for progesterone, busulfan is not found in the aqueous phase at a concentration above its solubility. Specifically, no crystals are visible by optical microscopy in the aqueous phase after encapsulation. Now, since busulfan is virtually insoluble in water, this indicates an incorporation of the busulfan into the nanocapsules.

B) Suspension of Busulfan (at a Concentration of 0.50 mg/ml)

A particle suspension at 0.50 mg/l is prepared under the same conditions as above after dissolving 50 mg of busulfan in 1 ml of N,N-dimethylacetamide. 175 mg of this solution are taken and added to 504 mg of Labrafac®. 75 mg of Lipoid® S75-3, 504 mg of Solutol®, 3.829 g of water and 88 mg of sodium chloride are also weighed out. The initial emulsion is thus at a concentration of 1.76 mg/ml of emulsion. The ingredients are combined in the same beaker and placed under magnetic stirring. Heat is applied until a temperature of 85° C. is reached. The system is allowed to cool to a temperature of 60° C. with magnetic stirring. This cycle (between 85° C. and 60° C.) is performed three times. At the final cooling, an quenching at 70° C. is carried out by adding 12.5 ml of distilled water at 2° C.±1° C. The system is then maintained under magnetic stirring for 5 minutes. The final concentration, i.e. after quenching, that is to say dilution, is 0.50 mg/ml.

EXAMPLE 5

Influence of the Nature of the Fatty Substance on the Phase Inversion Temperature Labrafac®, an oil composed of capric and caprylic acid triglycerides, is compared with fatty acid esters. It was possible to reveal the influence of the size of their end groups on the phase inversion temperature. An increase in the phase inversion temperature with increasing size of the groups is observed. Thus, in the myristate series, the change in appearance is visible at 69.5° C. for the ethyl ester, at 71.5° C. for the isopropyl ester and at 86.5° C. for the octyldodecyl ester. This increase means that an oil-in-water emulsion is more readily obtained when the oil has a lower HLB value (more lipophilic). Specifically, this more pronounced lipophilic nature brings about an accentuation of the hydrophobic bonds between the surfactant and the oil, and more energy is thus required to invert this system. Moreover, the carbon chain length of the fatty acid does not influence the particle size, or the phase inversion temperature (between $C_{14}$ and $C_{18}$). It appears, however, that the double bond present in ethyl oleate substantially increases the phase inversion temperature.

The results are given in the table below.

TABLE IV

| Oils | Number of carbons (fatty acid) | Double bonds | ° T change in appearance (° C.) | Particle size (nm) |
| --- | --- | --- | --- | --- |
| Labrafac ® lipophile | 8/10 | 0 | 77.0 | 43 ± 7 |
| Ethyl palmitate | 16 | 0 | 69.0 | 37 ± 15 |
| Ethyl oleate | 18 | 1 | 71.5 | 41 ± 5 |
| Ethyl myristate | 14 | 0 | 69.5 | 35 ± 13 |
| Isopropyl myristate | 14 | 0 | 71.5 | 44 ± 23 |
| Octyldodecyl myristate | 14 | 0 | 86.5 | 42 ± 16 |

The HLB value of the fatty substance does not appear to affect the particle size significantly.

EXAMPLE 6

Influence of the Nature of the Lipophilic Surfactant on the Size of the Nanocapsules Various types of lecithin whose phosphatidylcholine proportions range from 40% to 90% were used. The mean particle size increases as the phosphatidylcholine content in the lecithin increases (Table V below). Specifically, for 40% phosphatidylcholine, the size of the nanocapsules is 35±8 nm, whereas it is, respectively, 43±7 nm and 78±12 nm for a proportion of 75% and 90% phosphatidylcholine in the lecithin. On the other hand, the use of charged molecules did not allow nanocapsules to be obtained.

TABLE V

| Type of lipoid | % of phosphatidyl-choline | Mean particle size (nm) |
|---|---|---|
| Lipoid ® S45 | 40 | 35 ± 8 |
| Lipoid ® S75-3 | 69 | 43 ± 7 |
| Lipoid ® S100 | 90 | 78 ± 12 |
| Lipoid ® EPC | 98 | 61 ± 12 |
| Lipoid ® E80 | 80 | 72 ± 18 |

EXAMPLE 7

Lipid Nanocapsules with a Water-Soluble Active Principle Attached to their Surface 500 mg of a dispersion of lipid nanocapsules not containing active principle, as described in Example 1, are prepared using the following formulation:

| | |
|---|---|
| Lipoid ® S 75-3: | 1.51 mass % |
| Labrafac ® W1.1349: | 10.08 mass % |
| Solutol ® HS 15: | 10.08 mass % |
| Water: | 76.6 mass % |
| NaCl: | 1.76 mass % |

The lipid nanocapsules obtained have a size of 43±7 nm. 50 mg of the dispersion of lipid nanocapsules obtained are diluted in 1 ml of water and incubated with gentle stirring with an aqueous solution containing 50 µg of DNA (pSV β-galactosidase, Promega, France) for one hour in the presence of a mixture of histones obtained from calf thymus (Boehringer Mannheim, Germany). Lipid nanocapsules containing DNA molecules condensed with the proteins, adsorbed onto their surface, are obtained.

The invention claimed is:

1. A process for preparing nanocapsules comprising:
   (a) preparing a mixture in the form of an oil/water emulsion comprising an aqueous phase, an oily fatty phase comprising a fatty substance that is liquid or semiliquid at room temperature, and a lipophilic surfactant that is solid at 20° C.,
   (b) bringing about the phase inversion of said oil/water emulsion by at least two or more temperature cycles, wherein each temperature cycle comprises
      increasing the temperature up to a temperature $T_2$ above the phase inversion temperature (PIT) of the mixture to obtain a water/oil emulsion, followed by
      reducing the temperature to a temperature $T_1$, $T_1 < PIT < T_2$, to yield an oil/water emulsion as a translucent suspension, and
   (c) quenching the oil/water emulsion at approximately $T_1$ to obtain stable nanocapsules.

2. The process of claim 1, wherein the oily fatty phase further comprises a $C_8$ to $C_{12}$ triglyceride or a $C_8$ to $C_{18}$ fatty acid ester.

3. The process of claim 1, wherein the mixture further comprises a hydrophilic surfactant.

4. The process of claim 1, wherein the lipophilic surfactant is a lecithin whose phosphatidylcholine proportion is between 40% and 90%.

5. The process of claim 1, wherein the oil/water emulsion contains:
   1% to 3% of lipophilic surfactant,
   5% to 15% of hydrophilic surfactant,
   5% to 15% of fatty substance,
   64% to 89% of water,
   the percentages being expressed on a weight basis.

6. The process of claim 1, wherein the oil/water emulsion also contains from 1% to 4% of a salt.

7. The process of claim 1, wherein the lipophilic surfactant is solid at 37° C.

8. The process of claim 1, wherein the mixture further comprises a pharmaceutically active principle.

9. The process of claim 1, wherein the temperature of the quenching step is greater than $T_1$.

10. The process of claim 2 wherein the $C_8$ to $C_{12}$ triglyceride is selected from the group consisting of capric acid triglycerides, caprylic acid triglycerides, and mixtures thereof.

11. The process of claim 2, wherein the $C_8$ to $C_{18}$ fatty acid ester is selected from the group consisting of ethyl palmitate, ethyl oleate, ethyl myristate, isopropyl myristate, octyldodecyl myristate, and mixtures thereof.

12. The process of claim 4, wherein the lecithin is an oil composed of caprylic and capric acid medium-chain triglycerides.

13. The process of claim 6, wherein the salt is sodium chloride.

14. The process of claim 1, comprising carrying out on said oil/water emulsion at least three or more temperature cycles around the PIT.

15. The process of claim 14, wherein the fatty substance is a fatty acid triglyceride, the lipophilic surfactant is a lecithin, the hydrophilic surfactant is polyethylene glycol-6602-hydroxystearate, T1 is 60° C., T2 is 85° C., and the number of temperature cycles is equal to 3.

16. The process of claim 1, further comprising monitoring conductivity of the mixture during the temperature cycles.

17. The process of claim 3, wherein the hydrophilic surfactant is polyethylene glycol-6602-hydroxystearate.

18. The process of claim 8, wherein the pharmaceutically active principle is water soluble and is adsorbed onto the free surface of the stable nanocapsule.

* * * * *